US009658104B2

(12) United States Patent
Treado et al.

(10) Patent No.: US 9,658,104 B2
(45) Date of Patent: May 23, 2017

(54) SYSTEM AND METHOD FOR DETECTING UNKNOWN MATERIALS USING SHORT WAVE INFRARED HYPERSPECTRAL IMAGING

(71) Applicant: ChemImage Corporation, Pittsburgh, PA (US)

(72) Inventors: Patrick J. Treado, Pittsburgh, PA (US); Matthew Nelson, Harrison City, PA (US); Charles W. Gardner, Gibsonia, PA (US)

(73) Assignee: ChemImage Corporation, Pittsburgh, PA (US)

( * ) Notice: Subject to any disclaimer, the term of this patent is extended or adjusted under 35 U.S.C. 154(b) by 311 days.

(21) Appl. No.: 13/758,742

(22) Filed: Feb. 4, 2013

(65) Prior Publication Data

US 2013/0214162 A1 Aug. 22, 2013

Related U.S. Application Data

(63) Continuation-in-part of application No. 12/754,229, filed on Apr. 5, 2010, now Pat. No. 8,368,880.
(Continued)

(51) Int. Cl.
*G01N 21/00* (2006.01)
*G01J 3/28* (2006.01)
(Continued)

(52) U.S. Cl.
CPC . *G01J 3/28* (2013.01); *G01J 3/02* (2013.01); *G01J 3/0218* (2013.01); *G01J 3/32* (2013.01);
(Continued)

(58) Field of Classification Search
CPC ............. G01N 21/359; G01N 33/0057; G01N 21/3563; G01J 3/28; G01J 3/02; G01J 3/0218; G01J 3/32; G01J 3/44
(Continued)

(56) References Cited

U.S. PATENT DOCUMENTS 7,072,770 B1 * 7/2006 Schweitzer ............... G01J 3/28
702/22
2008/0225288 A1 * 9/2008 Rice .......................... G01J 3/44
356/301
(Continued)

OTHER PUBLICATIONS

Onat et al., "A Solid State Hyperspectral Imager for Real-time Standoff Explosives Detection using Shortwave Infrared Imaging", 2009, SPIE, vol. 7310, pp. 1-11.*
(Continued)

*Primary Examiner* — Hina F Ayub
(74) *Attorney, Agent, or Firm* — Pepper Hamilton LLP

(57) ABSTRACT

A system and method for analyzing unknown materials on surfaces including, but not limited to, chemical materials, biological materials, hazardous materials, drug materials, and non-threat materials using SWIR and/or extended range SWIR hyperspectral and spectroscopic techniques. A system comprising a collection optics, a tunable filter, and a first detector for generating a test data set representative of the unknown sample. A second detector, comprising a visible imaging device, may be configured to operate in a scanning mode to locate areas of interest for further interrogation using SWIR. A method comprising generating a SWIR test data set representative of the unknown sample and analyzing the unknown sample to detect, identify and/or distinguish an unknown material as a known material. This analysis may be achieved by comparing the test data set to a reference data set using at least one chemometric technique.

47 Claims, 7 Drawing Sheets

Related U.S. Application Data

(60) Provisional application No. 61/714,570, filed on Oct. 16, 2012.

(51) Int. Cl.

| | | |
|---|---|---|
| *G01J 3/02* | (2006.01) | |
| *G01J 3/44* | (2006.01) | |
| *G01N 21/359* | (2014.01) | |
| *G01J 3/32* | (2006.01) | |
| G01N 33/00 | (2006.01) | |
| G01N 21/3563 | (2014.01) | |

(52) U.S. Cl.
CPC .............. *G01J 3/44* (2013.01); *G01N 21/359* (2013.01); *G01N 21/3563* (2013.01); *G01N 33/0057* (2013.01)

(58) Field of Classification Search
USPC ..................................................... 356/72–73
See application file for complete search history.

(56) References Cited

U.S. PATENT DOCUMENTS

| | | | |
|---|---|---|---|
| 2010/0225899 A1* | 9/2010 | Treado et al. | 356/73 |
| 2011/0089323 A1* | 4/2011 | Treado et al. | 250/330 |
| 2011/0102565 A1* | 5/2011 | Wang et al. | 348/61 |
| 2012/0134582 A1* | 5/2012 | Treado et al. | 382/165 |
| 2012/0145906 A1* | 6/2012 | Treado et al. | 250/338.4 |
| 2012/0154792 A1* | 6/2012 | Treado et al. | 356/51 |
| 2013/0341509 A1* | 12/2013 | Nelson et al. | 250/330 |
| 2014/0042322 A1* | 2/2014 | Treado et al. | 250/339.01 |
| 2014/0043488 A1* | 2/2014 | Treado et al. | 348/164 |
| 2014/0183362 A1* | 7/2014 | Islam | G01J 3/453 250/338.4 |
| 2015/0185079 A1* | 7/2015 | Justice | G01J 3/2803 250/208.1 |

OTHER PUBLICATIONS

Scafi et al., "Identification of Counterfeit Drugs using Near-Infrared Spectroscopy", Nov. 2001, Analyst, vol. 126, pp. 2218-2224.*
Onat et al. ("A Solid-State Hyperspectral Imager for Real-time Standoff Explosives Detection using Shortwave Infrared Imaging", Proc. of SPIE vol. 7310, 2009).*

* cited by examiner

RGB Image      AN Fingerprint Detection Image

Ammonium Nitrate (AN) residue on the surface of a leather shoe at 50 m standoff range.

Detection of Ammonium Nitrate (AN) explosive material as it is deposited on the surface of a coffee cup at 30 meters range.

SYSTEM AND METHOD FOR DETECTING UNKNOWN MATERIALS USING SHORT WAVE INFRARED HYPERSPECTRAL IMAGING

RELATED APPLICATIONS

This application is a continuation-in-part of pending U.S. patent application Ser. No. 12/754,229, filed on Apr. 5, 2010, entitled "Chemical Imaging Explosives Optical (CHIMED) Sensor Using SWIR." This application also claims priority under 35 U.S.C. §119(e) to U.S. Provisional Patent Application No. 61/714,570, filed on Oct. 16, 2012, entitled "System and Method for Material Detection Using Short Wave Infrared Hyperspectral Imaging." These applications are hereby incorporated by reference in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, wide-field illumination may be used to collect spectra over the entire area encompassing the sample simultaneously using an electronically tunable optical imaging filter. Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the ultraviolet (UV), visible (VIS), near infrared (NIR), short-wave infrared (SWIR), extended range SWIR, mid infrared (MIR) wavelengths, and to some overlapping ranges. These correspond to wavelengths of about 180-380 nm (UV), about 380-700 nm (VIS), about 700-2500 nm (NIR), about 900-1700 nm (SWIR), about 1200-2500 nm (extended range SWIR) and about 2500-25000 nm (MIR).

There currently exists a need for accurate detection of unknown materials which may be threat materials such as biological, chemical, hazardous, and drug materials (including pharmaceutical and illegal drugs). Such a system and method may hold potential for detecting threat and other materials associated with individuals and their belongings in a wide variety of settings including, but not limited to: security checkpoints, points of inspection, transportation terminals, stadiums, traffic stops, security monitoring and other similar situations. There also exists a need for a system and method for the detection of such materials located in or on a person or an article associated with that person, including clothing items.

SUMMARY

The present disclosure relates to a system and method for analyzing unknown samples for potential threat materials such as chemical, biological, hazardous, and drug materials. More specifically, the present disclosure provides for analyzing unknown samples using SWIR (about 900-1700 nm) and/or extended range SWIR (about 1200-2500 nm) hyperspectral and/or spectroscopic techniques.

A system of the present disclosure may comprise at least one collection optics for collecting a plurality of interacted photons from an unknown sample. The interacted photons may be passed through a tunable filter and to a first detector for generating at least one test data set representative of the unknown sample. A second detector, such as a RGB video imaging device, may be used in a scanning mod to scan sample scenes and locate areas of interest for further interrogation using SWIR and/or extended range SWIR techniques.

A method of the present disclosure may comprise generating a test data set representative of the unknown sample, wherein the test data set comprises at least one of: a SWIR test data set and an extended range SWIR test data set. The test data set may comprise at least one of: a hyperspectral image and a spectrum representative of the unknown sample and may be analyzed to associate the unknown sample with a known sample.

The present disclosure also provides for a storage medium containing machine readable program code, which when executed by a processor causes the processor to perform the following: generate a test data set representative of an unknown sample wherein the test data set comprises at least one of: a SWIR test data set and an extended range SWIR test data set; and analyze the test data set to associate the unknown sample with a known sample.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE DISCLOSURE

Reference will now be made in detail to the preferred embodiments of the present disclosure, examples of which are illustrated in the accompanying drawings. Wherever possible, the same reference numbers will be used throughout the drawings to refer to the same or like parts.

The present disclosure provides for a system and method of analyzing unknown samples to detect, identify, and/or distinguish between threat and non-threat materials. In one embodiment, the unknown samples may comprise at least one of: a chemical material, a biological material, a hazardous material, a drug material (including but not limited to pharmaceutical and illegal drugs), and a non-threat material. Examples of drug materials that can be detected using the system and method of the present disclosure include, but are not limited to: marijuana, cocaine, ecstasy, aspirin, acetaminophen, caffeine, and cocaine. Spectra associated with these drug materials is illustrated in FIG. 1. In one embodiment, the present disclosure provides for the use of SWIR (about 900-1700 nm) and extended range SWIR (about 1200-2500 nm) hyperspectral and/or spectroscopic techniques to analyze the unknown materials.

Figure 1A:
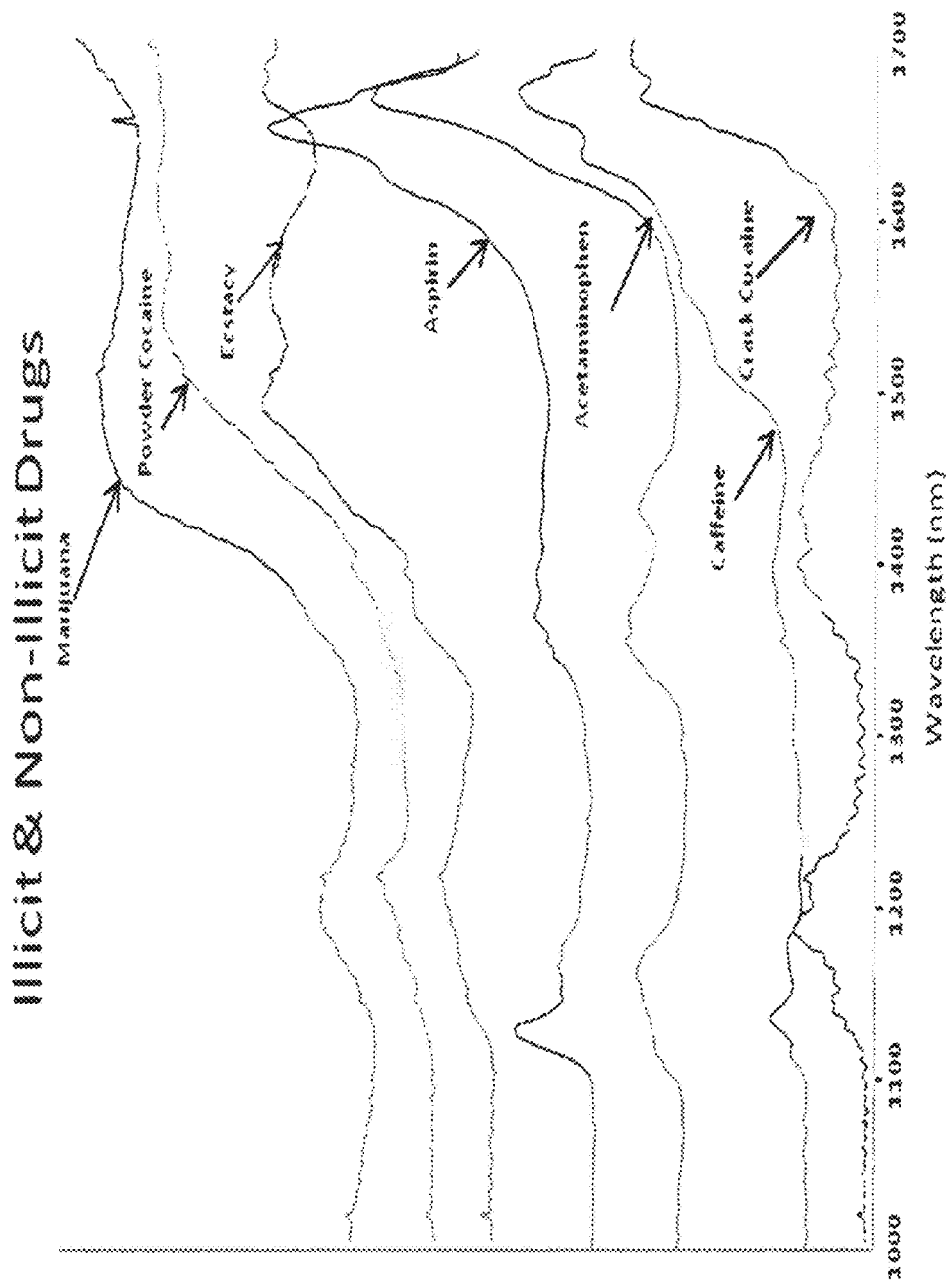
FIG. 1A is illustrative of representative drug spectra.
Figure 1B:
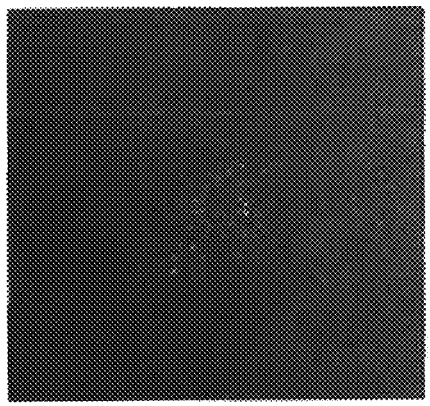
FIG. 1B is illustrative of the detection capabilities of the present disclosure.
Figure 1D:
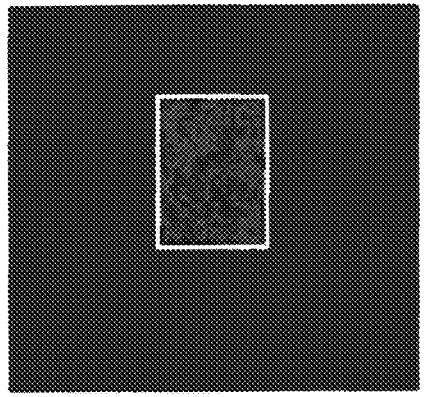
FIG. 1D is illustrative of the detection capabilities of the present disclosure.
Figure 1C:
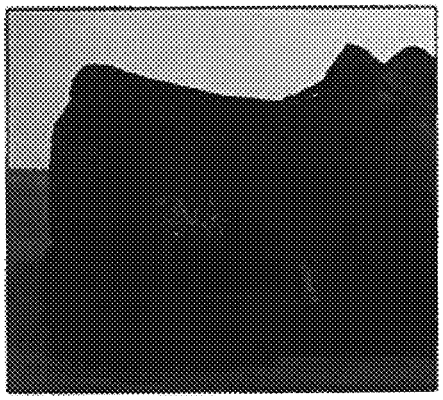
FIG. 1C is illustrative of the detection capabilities of the present disclosure.
Figure 1E:
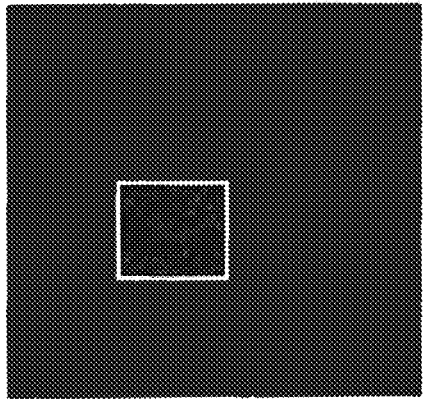
FIG. 1E is illustrative of the detection capabilities of the present disclosure.
Figure 1F:
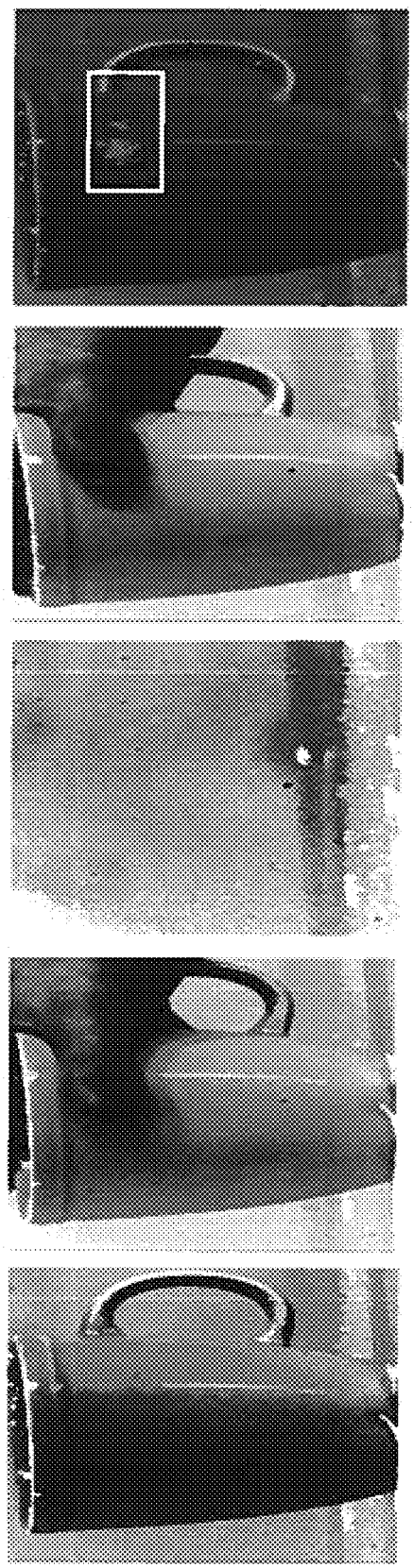
FIG. 1F is illustrative of the detection capabilities of the present disclosure.

In one embodiment, the unknown sample may be deposited on a surface such as a person, an object associated with a person, and a vehicle. The surface may comprise an object a person or the unknown sample has come in contact with such as a passport, a credit/debit card, a driver's license, a boarding pass, a ticket, a piece of clothing (including shoes, watches, jewelry or other wearable item), luggage, a wallet, a purse, and similar items. For example, FIGS. 1B and 1C illustrate the detection of explosive material on objects that may be in contact with a person or unknown sample. While these figures illustrate explosive detection, the present disclosure provides for the detection of other materials on similar surfaces. In one embodiment, the system and method may be configured to operate in a proximate, standoff, stationary, and/or On-the-Move (OTM) configurations. In another embodiment, the system and method may be configured to enable integration with LWIR, MM wave, and/or GPR sensors via industry standard fusion software. In another embodiment, the system and method may be configured to enable integration with other spectroscopic modalities.

Figure 2:
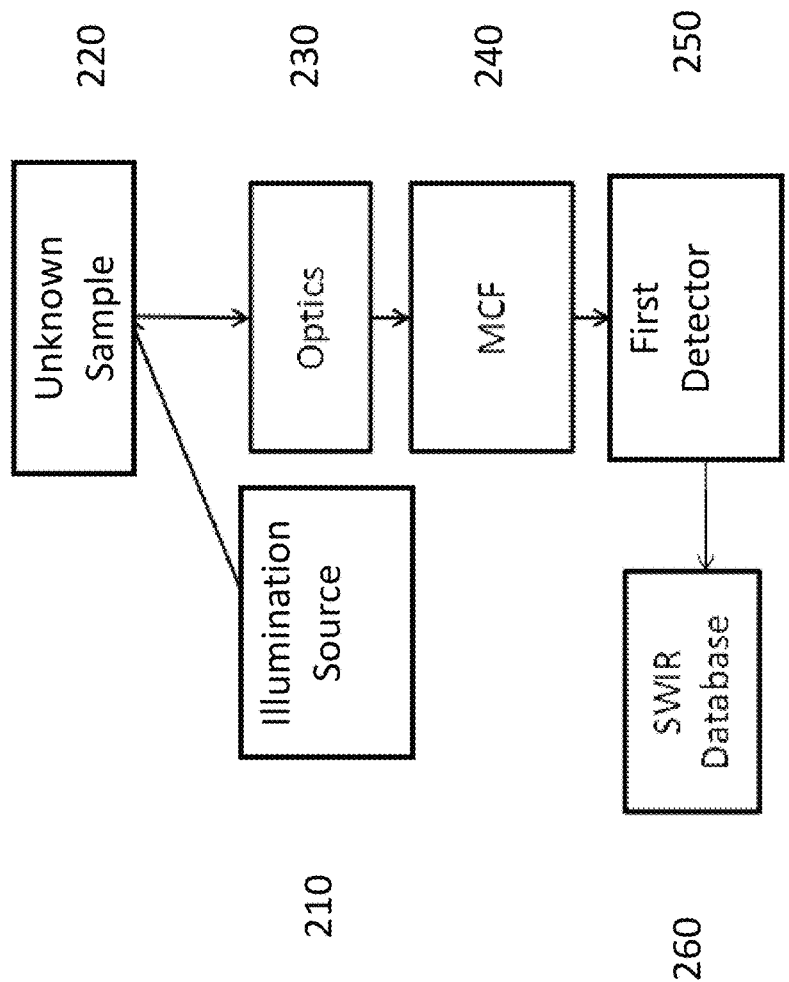
FIG. 2 is a schematic representation of a system of the present disclosure.

FIG. 2 is a schematic representation of a system of the present disclosure. In one embodiment, the system 200 may comprise at least one optic 230 for collecting interacted photons from an unknown sample 220. In one embodiment, the optics 230 may comprise a telescope optics configured for focusing and locating a first location and collecting the interacted photons. These interacted photons may comprise at least one of: photons absorbed by the unknown sample, photons reflected by the unknown sample, photons scattered by the known sample, and photons emitted by the unknown sample. In one embodiment, interacted photons may be generated by illuminating the unknown sample 220. This illumination may be achieved using at least one illumination source 210, which may comprise at least one of: an active illumination source and a passive illumination source. In one embodiment, the illumination source 210 may comprise at least one of: a laser light source, a broadband light source, and an ambient light source. In an embodiment comprising passive illumination, the system 200 may be configured to operate with solar radiation as an illumination source. In one embodiment, wide-field illumination may be used.

Interacted photons generated from the unknown sample may be passed through a tunable filter 240 to filter the interacted photons into a plurality of wavelength bands. In one embodiment, the tunable filter 240 may be configured to sequentially filter the interacted photons. The plurality of predetermined wavelength bands may include specific wavelengths or ranges of wavelengths that correspond to known materials of interest.

The interacted photons may be detected by a first detector 250 to generate at least one test data set representative of the unknown sample. In one embodiment, the first detector 250 may comprise at least one of: an InGaAs detector, a CCD detector, a CMOS detector, an InSb detector, and a MCT detector. In one embodiment, the test data set may comprise at least one of: a SWIR data set and an extended range SWIR data set. The test data set may comprise at least one of: a hyperspectral image and a spectrum. In one embodiment where the test data set comprises a hyperspectral image, spectral information may be extracted from one or more regions of interest of the image.

The system may further comprise a processor which may be configured to operate various component parts of the system, process test data, provide for user control, and store test and/or reference data. This reference data may be stored in a reference data base 260 comprising at least one reference data set, where each reference data set is associated with a known sample. The processor may also be configured to compare test data with reference data. In one embodiment, the processor may comprise machine readable program code when may be executed to carry out the various system functions.

In one embodiment, the system 200 may further comprise a second detector configured to operate in a scanning mode and output an image that can be used to identify locations of interest in a sample scene. These regions of interest may then be interrogated using SWIR and/or extended range SWIR techniques. In one embodiment, the second detector may comprise a visible imaging device, such as a RGB visible imaging device. This visible imaging device may comprise a RGB video imaging device.

Figure 3:
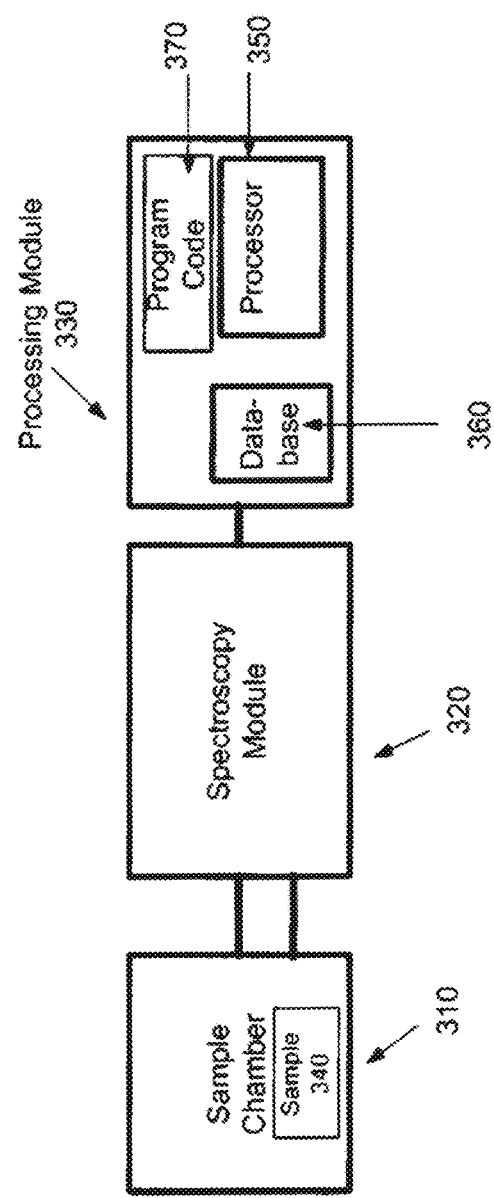
FIG. 3 is a schematic representation of a system of the present disclosure.

FIG. 3 illustrates a second exemplary system 300 of the present disclosure. Sensor system 300 includes sample chamber 310, spectroscopy module 320 and processing module 330. Sample 340 is placed inside sample chamber 310 for analysis. Processing module 330 includes processor 350, database 360, and machine readable program code 370. Database 360 may comprise at least one reference data set associated with a known material.

Spectroscopy module 320 may include one or more detectors. In one embodiment, spectroscopy module 320 may include at least one of: an InGaAs detector, a CCD detector, a CMOS detector, an InSb detector, and a MCT detector. The machine readable program code 370 may comprise executable program instructions. Processor 350 is may be configured to execute the machine readable program code 370 so as to perform the methods of the present disclosure. In one embodiment, processor 350 may be configured to execute a machine readable program code 370 to search database 360. The database 360 can be searched using a variety of similarity metrics or chemometric techniques. In one embodiment, the similarity metric produces a score.

Figure 4A:
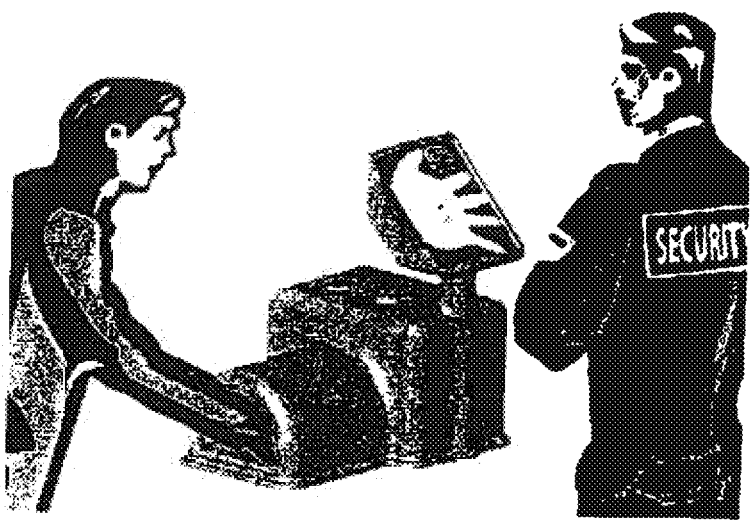
FIG. 4A is illustrative of a mode of use of a system of the present disclosure.
Figure 4B:
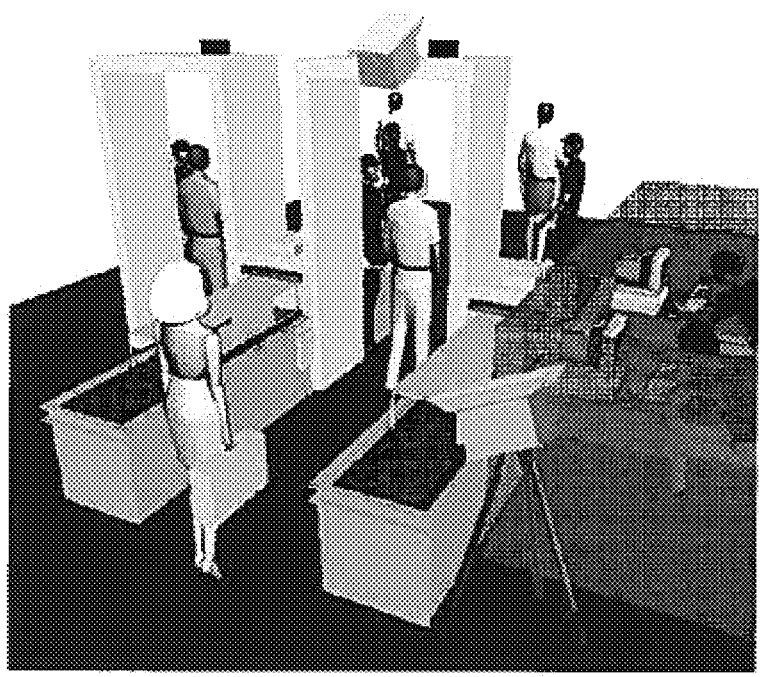
FIG. 4B is illustrative of a mode of use of a system of the present disclosure.

FIG. 4A illustrates an exemplary mode of use of a system of the present disclosure. In such an embodiment, an unknown sample (shown in FIG. 4A as a human hand) may be placed in sample chamber for analysis. A user (shown in FIG. 4A as a security officer) may analyze the hyperspectral information generated. In FIG. 4B, individuals and their belongings may be screened at a standoff distance for covert screening. The modes of use on FIGS. 4A and 4B hold potential for screening individuals and their belongings while passing though a security checkpoint.

Figure 5:
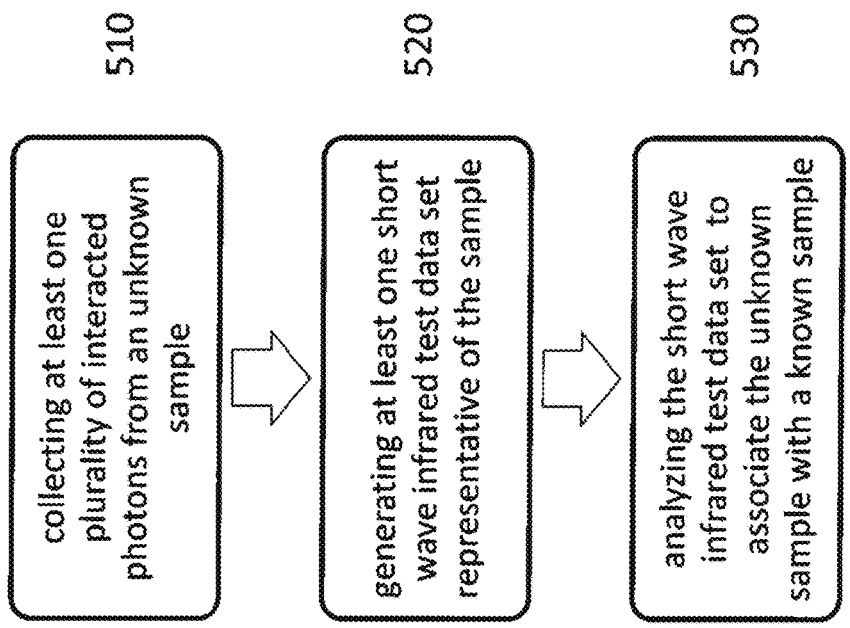
FIG. 5 is representative of a method of the present disclosure.

FIG. 5 is illustrative of a method of the present disclosure. In one embodiment, the method 500 provides for collecting at least one plurality of interacted photons from an unknown sample in step 510. The present disclosure contemplates the sample may comprise at least one of: a chemical material, a biological material, a hazardous material, a drug material, and a non-threat material. The interacted photons may be generated by illuminating the sample using at least one of active illumination and passive illumination. In one embodiment, wide-field illumination may be used. The interacted photons may be passed through a tunable filter to filter the interacted photons into a plurality of wavelength bands.

In one embodiment, the method 500 may comprise scanning a sample scene to locate the unknown sample. This scanning may comprise generating a visible image of a first location (the sample scene) and analyzing the visible image (such as a RGB video image) to identify a second location comprising the unknown sample. Morphological features, such as size, color, and shape, and the location of objects in the visible image may aid a user in selecting a second location for further inspection. For example, when scanning a sample scene of a crowded airport, a user may select a second location comprising a piece of luggage for further inspecting using SWIR techniques.

In step 520 at least one test data set representative of the sample may be generated. In one embodiment, the test data set may comprise at least one of: a SWIR test data set and an extended range SWIR test data set. The test data set may be analyzed in step 530 to associate the unknown sample with a known sample. In one embodiment, the analyzing in step 530 may further comprise comparing the test data set with at least one reference data set associated with a known sample. This comparing may be achieved using at least one chemometric technique. Examples of chemometric techniques that may be applied include, but are not limited to: correlation analysis, principle component analysis, principle component regression, partial least squares, multivariate curve resolution, Mahalanobis distance, Euclidian distance, band target entropy, band target energy minimization, partial least squares discriminant analysis, adaptive subspace detection, and combinations thereof.

In one embodiment, the present disclosure also provides for a storage medium containing machine readable program code, which when executed by a processor causes the processor to perform the following: generate a test data set representative of a unknown sample, wherein the test data set comprises at least one of: a SWIR test data set and an extended range SWIR test data set. The storage medium, when executed by a processor to analyze the test data set may further cause the processor to compare the test data set with at least one reference data set associated with a known sample. In one embodiment, this comparison may be achieved by applying at least one chemometric technique. The storage medium may when executed by a processor to generate the test data set may further cause the processor to configure a tunable filter to filter a plurality of interacted photons into a plurality of wavelength bands.

While the disclosure has been described in detail in reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method comprising:
  collecting a plurality of interacted photons from an unknown sample;
  generating a first test data set from a first detector, the first data set comprising a short-wave infrared hyperspectral image from a first plurality of the plurality of interacted photons collected at wavelengths ranging from about 900-1,700 nm;
  generating a second test data set from the first detector, the second data set comprising an extended short-wave infrared hyperspectral image from a second plurality of the plurality of interacted photons collected at wavelengths ranging from about 1,200-2,500 nm; and
  analyzing the first test data set and the second test data set to associate the unknown sample with a known sample.

2. The method of claim 1, wherein the plurality of interacted photons are generated by illuminating the unknown sample.

3. The method of claim 2, wherein illuminating the unknown sample comprises applying wide-field illumination.

4. The method of claim 2, wherein the illuminating comprises at least one of active illumination and passive illumination.

5. The method of claim 1, further comprising passing the plurality of interacted photons through a tunable filter configured to filter the interacted photons into a plurality of wavelength bands.

6. The method of claim 5, wherein the tunable filter further comprises one or more of a multi-conjugate tunable filter, a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot tunable filter, and a liquid crystal Fabry Perot tunable filter.

7. The method of claim 1, wherein the unknown sample comprises one or more of a chemical material, a biological material, a hazardous material, a drug material, and a non-threat material.

8. The method of claim 7, wherein the drug material comprises one or more of a pharmaceutical drug and an illegal drug.

9. The method of claim 1, wherein the unknown sample comprises a material deposited on a surface.

10. The method of claim 9, wherein the surface comprises one or more of a part of a person, a part of an object associated with a person, and a part of a vehicle.

11. The method of claim 10, wherein the object associated with a person comprises one or more of a passport, a credit card, a driver's license, a boarding pass, a piece of clothing, a human-wearable item, a shoe, luggage, a purse, a wallet, and an airline ticket.

12. The method of claim 10, wherein the object associated with a person comprises an object that has contacted the person.

13. The method of claim 1, further comprising:
generating at least one visible image representative of a first location; and
analyzing the visible image to identify a second location comprising the unknown sample.

14. The method of claim 13, wherein the visible image comprises an RGB video image.

15. The method of claim 1, wherein the analyzing comprises comparing the first test data set and the second test data set with at least one reference data set, wherein each reference data set is associated with a known sample.

16. The method of claim 15, wherein the comparing comprises applying at least one chemometric technique.

17. The method of claim 16, wherein the chemometric technique comprises one or more of a correlation analysis, a principle component analysis, a principle component regression analysis, a partial least squares analysis, a multivariate curve resolution analysis, a Mahalanobis distance analysis, an Euclidian distance analysis, a band target analysis, an entropy analysis, a hand target energy minimization analysis, a partial least squares discriminant analysis, an adaptive subspace detection analysis and combinations thereof.

18. The method of claim 1, wherein the analyzing further comprises extracting at least one spectrum from one or more of the first test data set and the second test data set.

19. A system comprising:
a collection optic configured to collect a plurality of interacted photons from an unknown sample;
a tunable filter configured to filter the plurality of interacted photons into a plurality of filtered photons comprising a plurality of wavelength bands;
a first detector configured to detect a first plurality of the plurality of filtered photons and generate a first test data set comprising a short-wave infrared hyperspectral image collected at wavelengths ranging from about 900-1,700 nm and detect a second plurality of the plurality of filtered photons and generate a second test data set comprising an extended short-wave infrared hyperspectral image collected at wavelengths ranging from about 1,200-2,500 nm.

20. The system of claim 19, wherein the unknown sample comprises one or more of a chemical material, a biological material, a hazardous material, a drug material, and a non-threat material.

21. The system of claim 19, wherein the unknown sample comprises a drug material selected from the group consisting of a pharmaceutical drug and an illegal drug.

22. The system of claim 19, wherein the unknown sample comprises a material deposited on a surface.

23. The system of claim 22, wherein the surface comprises one or more of a part of a person, a part of an object associated with a person, and a part of a vehicle.

24. The system of claim 23, wherein the object associated with a person comprises one or more of a passport, a credit card, a driver's license, a boarding pass, a piece of clothing, a human-wearable item, a shoe, luggage, a purse, a wallet, and an airline ticket.

25. The system of claim 23, wherein the object associated with a person comprises an object that has contacted the person.

26. The system of claim 19, further comprising a second detector configured to scan a first location comprising the unknown sample.

27. The system of claim 26, wherein the second detector comprises a visible imaging device.

28. The system of claim 27, wherein the visible imaging device comprises an RGB video imaging device.

29. The system of claim 19, wherein the tunable filter further comprises one or more of a multi-conjugate tunable filter, a Fabry Perot angle tuned filter, an acousto-optic tunable filter, a liquid crystal tunable filter, a Lyot filter, an Evans split element liquid crystal tunable filter, a Solc liquid crystal tunable filter, a fixed wavelength Fabry Perot tunable filter, an air-tuned Fabry Perot tunable filter, a mechanically-tuned Fabry Perot, tunable filter, and a liquid crystal Fabry Perot tunable filter.

30. The system of claim 19, wherein the collection optic further comprises a telescope optic.

31. The system of claim 19, further comprising a reference database comprising at least one reference data set associated with a known material.

32. The system of claim 31, wherein the reference data set comprises one or more of a hyperspectral image and a spectrum.

33. The system of claim 19, wherein the system is further configured to operate with one or more of an active illumination source and a passive illumination source.

34. The system of claim 33, wherein the active illumination source comprises one or more of a laser light source and a broadband light source.

35. The system of claim 33, wherein the passive illumination source comprises one or more of solar radiation and ambient light.

36. The system of claim 19, further comprising a wide-field illumination source configured to generate the plurality of interacted photons.

37. The method of claim 19, wherein the first detector comprises one or more of an InGaAs detector, a CCD detector, a CMOS detector, an InSb detector, and a MCT detector.

38. A storage medium containing machine readable program code, which, when executed by a processor, causes the processor to perform the following:
generate a first test data from a first detector, the first data set comprising a short-wave infrared hyperspectral image collected at wavelengths ranging from about 900-1,700 nm and a second data set from the first detector, the second data set comprising an extended range short-wave infrared hyperspectral image data set collected at wavelengths ranging from about 1,200-2,500 nm; and
analyze the first test data set and the second test data set to associate the unknown sample to a known material.

39. The storage medium of claim 38, which when executed by a processor to analyze the first test data set and second test data set, causes the processor to compare the first test data set and the second test data set with at least one reference data set, wherein each reference data set is associated with a known material.

40. The storage medium of claim 39, which when executed by a processor to compare the first test data set and the second test data set with a reference data set causes the processor to apply at least one chemometric technique.

41. The storage medium of claim 38, which when executed by a processor to generate the test data set further causes the processor to configure a tunable filter to filter a plurality of interacted photons collected from the unknown sample into a plurality of wavelength bands.

42. The storage medium of claim 38, wherein the unknown sample comprises one or more of a chemical material, a biological material, a hazardous material, a drug material, and a non-threat material.

43. The storage medium of claim 38, wherein the unknown sample comprises a drug material selected from the group consisting of a pharmaceutical drug and an illegal drug.

44. The storage medium of claim 38, wherein the unknown sample comprises a material deposited on a surface.

45. The storage medium of claim 44, wherein the surface comprises one or more of a part of a person, an object associated with a person, and a part of a vehicle.

46. The storage medium of claim 45, wherein the object associated with a person comprises one or more of a passport, a credit card, a driver's license, a boarding pass, a piece of clothing, a human-wearable item, a shoe, luggage, a purse, a wallet, and an airline ticket.

47. The storage medium of claim 45, wherein the object associated with a person comprises an object that has contacted the person.

* * * * *